(12) United States Patent
Parks

(10) Patent No.: US 7,351,233 B2
(45) Date of Patent: Apr. 1, 2008

(54) SUBCUTANEOUS VASCULAR ACCESS PORT, NEEDLE AND KIT, AND METHODS OF USING SAME

(76) Inventor: Robert A. Parks, 298 Ann St., Plymouth, MI (US) 48170

( * ) Notice: Subject to any disclaimer, the term of this patent is extended or adjusted under 35 U.S.C. 154(b) by 515 days.

(21) Appl. No.: 10/965,514

(22) Filed: Oct. 14, 2004

(65) Prior Publication Data

US 2005/0085778 A1  Apr. 21, 2005

Related U.S. Application Data

(60) Provisional application No. 60/511,152, filed on Oct. 14, 2003.

(51) Int. Cl.
  *A61M 31/00* (2006.01)
(52) U.S. Cl. ................................. 604/288.01
(58) Field of Classification Search ........... 604/93, 604/175, 244, 256, 267, 241, 242, 243, 288.01, 604/288.02, 288.03, 288.04, 94.01, 95.01, 604/95.02–95.05
  See application file for complete search history.

(56) References Cited

U.S. PATENT DOCUMENTS

| | | |
|---|---|---|
| 4,326,530 A | 4/1982 | Fleury, Jr. |
| 4,929,236 A | 5/1990 | Sampson |
| 5,053,013 A | 10/1991 | Ensminger et al. |
| 5,092,849 A | 3/1992 | Sampson |
| 5,176,641 A | 1/1993 | Idriss |
| 5,180,365 A | 1/1993 | Ensminger et al. |
| 5,263,930 A | 11/1993 | Ensminger |
| 5,281,205 A * | 1/1994 | McPherson ................. 604/267 |
| 5,338,301 A | 8/1994 | Diaz |
| 5,356,381 A * | 10/1994 | Ensminger et al. .... 604/288.03 |
| 5,456,675 A * | 10/1995 | Wolbring et al. .......... 604/537 |
| 5,741,228 A * | 4/1998 | Lambrecht et al. .... 604/288.01 |
| 5,743,873 A | 4/1998 | Cai et al. |
| 6,039,712 A | 3/2000 | Fogarty et al. |

(Continued)

OTHER PUBLICATIONS

Popper & Sons, Inc., Catalog, Oct. 12, 2007, pp. 1-38, Source: www.popperandsons.com (Attached all 38 pages).
Epidural Needles, Oct. 12, 2007, p. 1, Source: http://www.spectramedical.com/epidural.html, (Attached 1 page).

*Primary Examiner*—Manuel Mendez
(74) *Attorney, Agent, or Firm*—Carrier, Blackman & Associates, P.C.; William D. Blackman; Joseph P. Carrier

(57) ABSTRACT

A surgically implantable access port has a main port body with an internal chamber formed therein, and an outlet tube connected to the main port body. The internal chamber is configured to readily receive a guide wire therein, and to passively direct the tip of a guide wire to an outlet, which is in fluid communication with the outlet tube. The chamber in the main port body is formed in a directionally aimed conical shape. The outlet may be located at the lowest area of the chamber, to help direct a guide wire thereto. A specialized needle is also described, having a curved tip with an opening formed therein. The top inner surface and the bottom outer surface of the needle, adjacent the tip opening, are rounded and non-sharp to avoid damaging a guide wire or catheter when used therewith. Methods of using the port and needle are also disclosed.

18 Claims, 13 Drawing Sheets

U.S. PATENT DOCUMENTS 6,186,987 B1 * 2/2001 Grooters ............... 604/264
6,203,552 B1   3/2001 Bagley et al.
6,290,677 B1   9/2001 Arai et al.
6,613,013 B2   9/2003 Haarala et al.

* cited by examiner

PRIOR ART

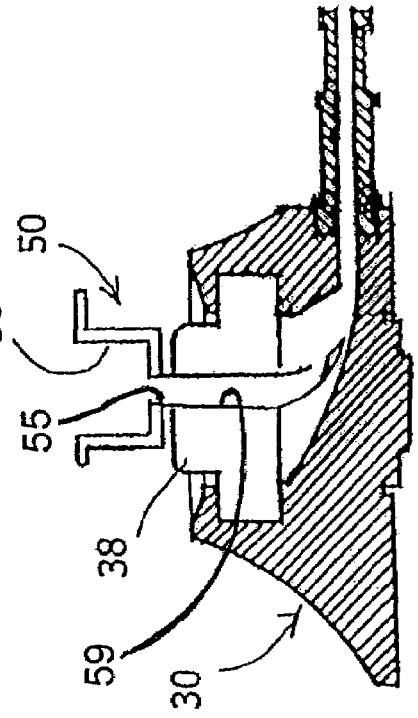
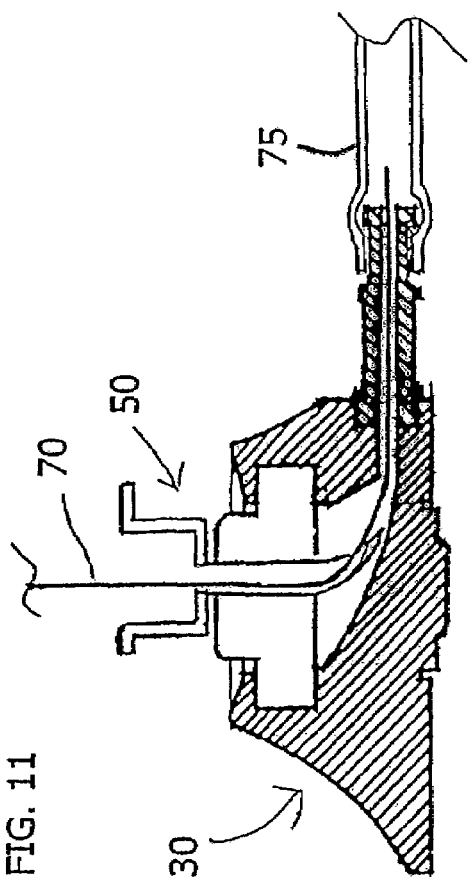
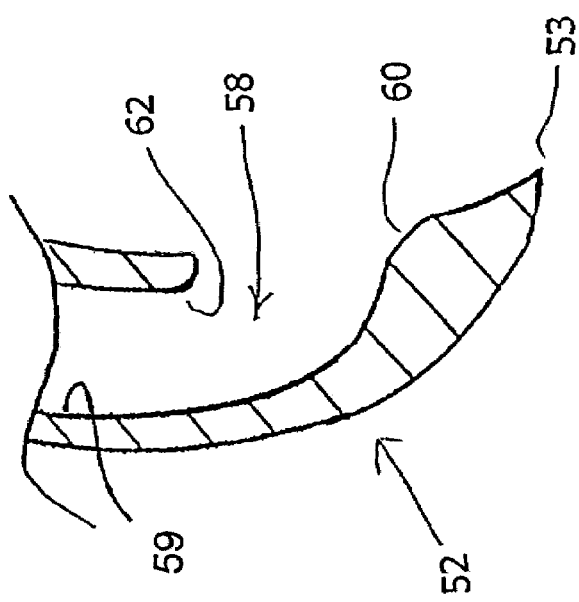

FLIPPED CATH.

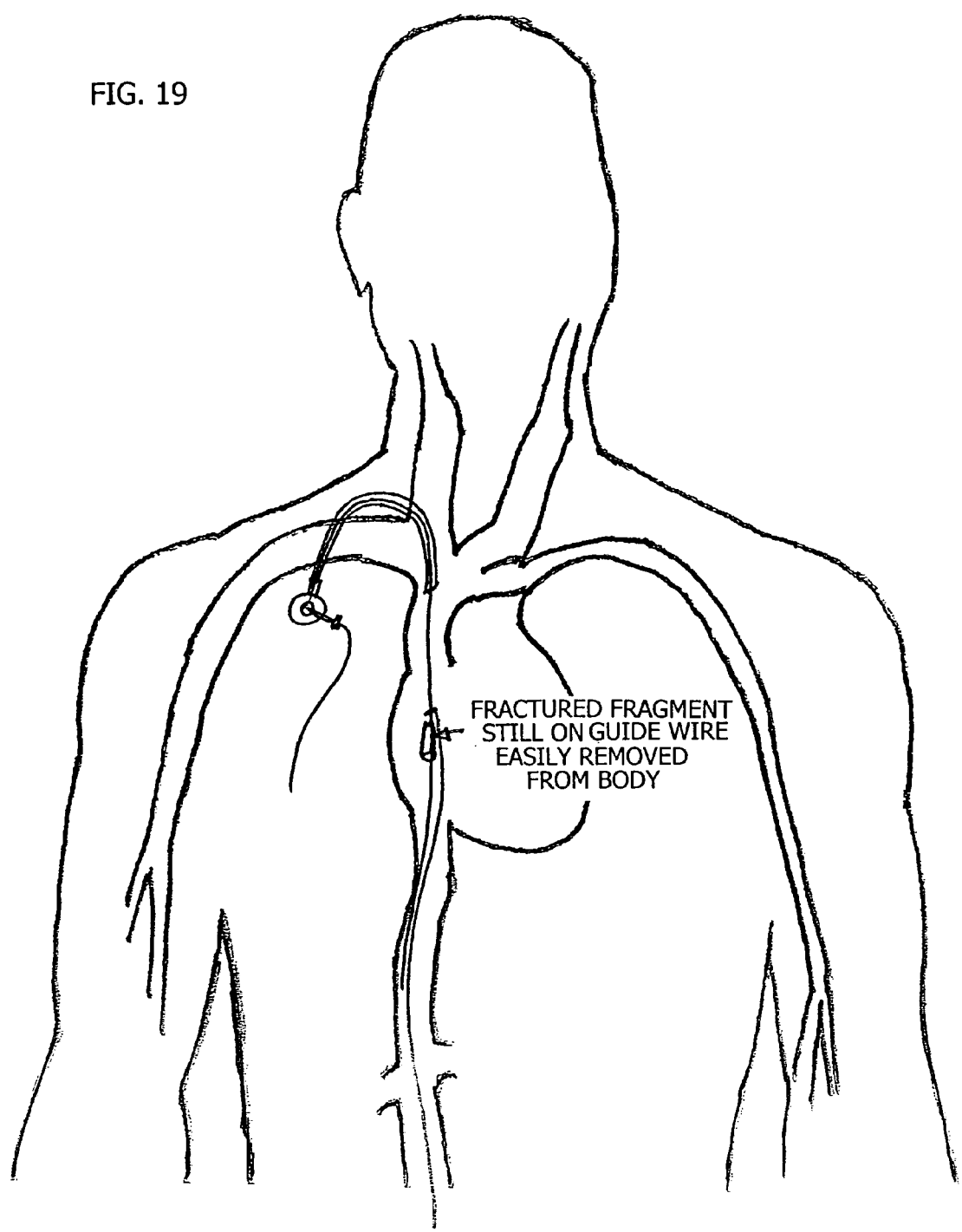

SUBCUTANEOUS VASCULAR ACCESS PORT, NEEDLE AND KIT, AND METHODS OF USING SAME

CROSS-REFERENCE TO RELATED APPLICATIONS

The present invention claims priority under 35 USC 119 based on U.S. provisional patent application No. 60/511,152, filed Oct. 14, 2003. The complete disclosure of the referenced provisional application is incorporated herein by reference.

BACKGROUND OF THE INVENTION

1. Field of the Invention

The present invention relates to implantable subcutaneous vascular access ports, for implanting beneath the skin of a patient, and for allowing vascular access for medicines to be repeatedly injected into a patient, or for drawing blood, without damaging the access site. More particularly, the present invention relates to a subcutaneous vascular access port having a uniquely-shaped internal chamber therein.

2. Description of the Background Art

A number of different implantable subcutaneous vascular access ports are known, for allowing a medical professional to repeatedly inject medicine into a patient over time. This is useful, for example, in a patient who is receiving chemotherapy treatment for cancer. Examples of some brand names for known implantable subcutaneous vascular access ports include X-Port™, Port-A-Cath®, and Vortex™. A number of these known access ports are manufactured and sold by the C. R. Bard Company of Murray Hill, N.J.

Examples of some of the known implantable subcutaneous vascular access ports include those disclosed in U.S. Pat. Nos. 4,929,236, 5,053,013, 5,092,849, 5,180,365, 5,176,641, 5,263,930, 5,743,873, 6,039,712, 6,290,677, and 6,613,013, as well as the references cited in each of these patents.

A generic example of a known prior art access port is shown in cross-section in FIGS. 1 and 2. This known port apparatus 10 includes a main port body 12 having a hollow chamber 14 formed therein. The chamber 14 is substantially cylindrical in shape, and has a substantially flat floor 16. The known access port also includes a flexible septum 18, attached to the main port body 12 and covering the hollow chamber 14. The septum 18 is formed from a resiliently deformable material such as a silicone elastomer.

The access port 10 of FIGS. 1-2 also includes a hollow outlet tube 20, attached to the main port body 12 and in fluid communication with the hollow chamber 14 thereof, via an outlet aperture 22 formed in a side wall of the main port body 12, at a location spaced above the floor 16 thereof, as shown.

Where used, one of the known implantable subcutaneous vascular access ports 10 is implanted beneath the skin of a patient's upper chest or arm, with a proximal end 21 of a catheter 24 connected to the outlet tube 20 of the device. The other, distal end of the catheter 24 is fed through the internal jugular vein, subclavian vein or arm vein, respectively, and into the central venous system. The access port 10 and the attached catheter 24 are left in place inside of the patient's body for a period of time, which may be a number of years, in some cases.

After the port apparatus 10 and attached catheter 24 are in place in the patient, a medical professional first confirms the location of the port, and also confirms that the catheter is in the venous system. Then, the appropriate skin surface is cleaned, and the medical professional is able to withdraw blood and/or inject medicine into the patient, by inserting the tip of a hypodermic needle through the overlying skin, through the septum 18 of the device, and into the chamber beneath the septum, and subsequently drawing blood or dispensing the medicine into the patient's bloodstream via the catheter.

As noted above, the access port and the attached catheter remain inside of the patient's body for a period of time. Over time, tissue may form around the port body 12, helping to embed it in place.

As time passes with the access port and catheter implanted inside the patient's body, the body's natural immune system may accumulate antibodies, myelin, fibrin and/or other materials from the blood on the tip of the catheter, which can eventually form a sheath over the catheter. This sheath can obstruct or even block fluid flow through the catheter. After such time, it often becomes necessary to follow a sequence of steps to remove the sheath, in order to clean the tip end of the catheter and resume normal operation.

When such blockage is suspected, it is normal practice to inject a dye into the access port 10. The dispersion pattern of the dye may be viewed on an X-ray of the affected area, which will enable a physician to determine whether or not the catheter tip is blocked with a sheath.

If a sheath is found to be blocking the distal end of the catheter 24, it has previously been the practice, in such an instance, to open a femoral vein and to insert a loop snare thereinto, and to advance the working end of the loop snare to the location of the sheath.

Examples of known snares usable for this purpose are described in U.S. Pat. Nos. 6,203,552 and 4,326,530, the disclosures of which are hereby incorporated by reference. The loop of the snare is then placed around the sheath-covered catheter and the loop is then manually tightened around the sheath and catheter. The sheath is then pulled off the catheter, by carefully withdrawing the loop snare while it holds the sheath.

It has been discovered that during the conventional procedure described above, a number of complications can arise.

The wire loop portion of the loop snare can be sharp, and if it is tightened too aggressively, the wire loop can cut off the tip of the catheter, which then floats uncontrolled in the bloodstream. Another complication can arise while withdrawing the loop snare, because the distal end of the catheter may break off, in response to pulling pressure, instead of releasing the sheath. The broken catheter tip then becomes a floating hazard in the bloodstream.

In either scenario discussed in the proceeding paragraph, a loose piece of the catheter tip, which has been fractured from the distal end of the catheter, becomes a foreign body which may float freely in the bloodstream, and will eventually lodge in the heart or lung, where it causes a blockage. In such a situation, further medical intervention, up to and including surgery may be necessitated, in order to retrieve the broken-off catheter tip.

Therefore, a method and apparatus is needed for reducing the risk of a tip portion of a catheter becoming loose in a patient's vascular system.

Although the known devices have some utility for their intended purposes, a need still exists in the art for an improved implantable access port, and for a method of removing a sheath from a catheter tip connected to an access port. In particular, there is a need for an improved method which will anticipate, and provide for controlled movement of a catheter fragment, in a situation where a catheter tip breaks off of a catheter during a sheath-removal procedure.

SUMMARY OF THE INVENTION

The present invention provides an improved implantable access port, having a main port body with an internal chamber formed therein, in which the internal chamber is configured to readily receive a guide wire therein, and to direct the tip of the guide wire to an outlet. Optionally, the chamber in the main port body may be formed in a directionally aimed conical shape, similar to the shape of a bubble pipe bowl, or an old-fashioned ear trumpet. The central axis of the chamber curves approximately ninety degrees from the inlet to the outlet of the access port.

Accordingly, it is an object of the present invention to provide an improved implantable access port assembly, and a method of using same. It is another object of the present invention to provide an access port assembly and method in which the internal chamber of the access port is configured to passively direct the tip of a guide wire to an outlet thereof.

The invention also relates to a specialized needle, having a curved tip with an opening formed therein. The top inner and the bottom outer surfaces of the needle, adjacent the tip opening, are made non-sharp to avoid damaging a guide wire when used therewith.

According to one aspect of the invention, a kit may be provided which includes an access port and a specialized needle. Optionally, the kit may also include a guide wire.

For a more complete understanding of the present invention, the reader is referred to the following detailed description section, which should be read in conjunction with the accompanying drawings. Throughout the following detailed description and in the drawings, like numbers refer to like parts.

BRIEF DESCRIPTION OF THE DRAWINGS

FIG. 9 is a sagittal cross-section of the needle tip of FIG. 8;

FIG. 10 is a sagittal cross-section of the access port apparatus of FIG. 3, with the needle apparatus of FIG. 7 inserted therein;

FIG. 11 is a sagittal cross-section similar to that of FIG. 10, also showing a guide wire being slidably inserted through the needle apparatus and into a catheter;

FIG. 19 is another simplified diagram of a patient's central venous system similar to FIG. 12, showing how the position of a broken fragment is controlled during a procedure according to the present invention.

DETAILED DESCRIPTION

Figure 1:
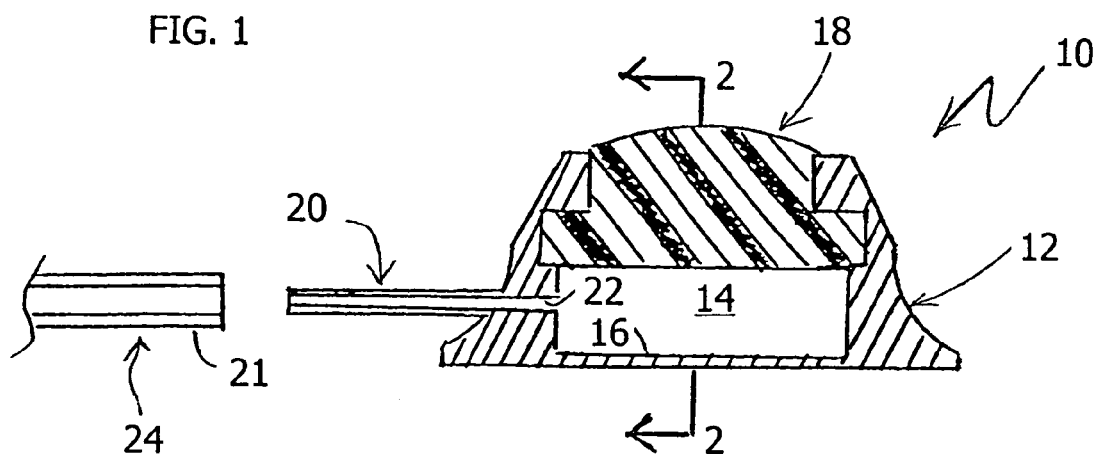
FIG. 1 is a sagittal cross-sectional view of an access port apparatus according to a prior art design.

Throughout the present specification, relative positional terms like 'upper', 'lower', 'front', 'rear', 'top', 'bottom', 'horizontal', 'vertical', and the like are used to refer to the orientation of the apparatus as shown in the drawings. These terms are used in an illustrative sense to describe the depicted embodiments, and are not meant to be limitative. It will be understood that the depicted apparatus may be placed at an orientation different from that shown in the drawings, such as inverted 180 degrees or transverse to that shown, and in such a case, the above-identified relative positional terms will no longer be accurate. In fact, while the access port hereof is shown and discussed in one possible orientation thereof, it will be understood that when surgically installed in a patient, the access port may be oriented differently from the orientation shown in some of the Figures.

Referring now to FIGS. 3-6, an implantable access port apparatus, according to a selected illustrative embodiment of the present invention, is shown generally at 30.

According to one aspect of the invention, a kit may be provided which includes an access port 30 and a specialized needle 50 (FIG. 7), to be discussed subsequently. Optionally, the kit may also include a guide wire 70 (FIG. 11).

Structure of the Access Port Apparatus

The access port apparatus 30 of FIGS. 3-6 includes a main port body 32 having a hollow chamber 34 formed therein. The main port body 32 is formed generally in a truncated conical shape with a flat top, modified to have one flat side, as shown. The bottom of the main port body 32 is generally flattened.

The main port body 32 has an annular channel 33 formed therein above the chamber 34, to receive an edge portion of a septum 38 therein. The main port body 32 is formed from a biocompatible material, such as titanium, a titanium alloy or another biocompatible corrosion-resistant metal, or from a strong biocompatible plastic. Where plastic is used for the main port body 32, a titanium liner may be provided for placement inside of the chamber 34.

Figure 4:
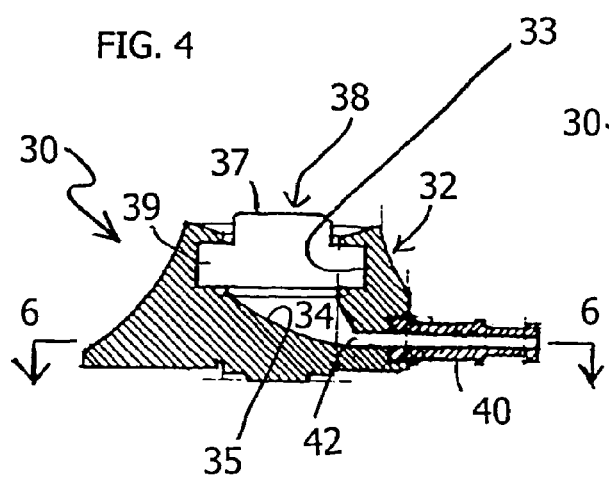
FIG. 4 is a sagittal cross-sectional view of the access port apparatus of FIG. 3, taken along the line 4-4 therein.
Figure 5:
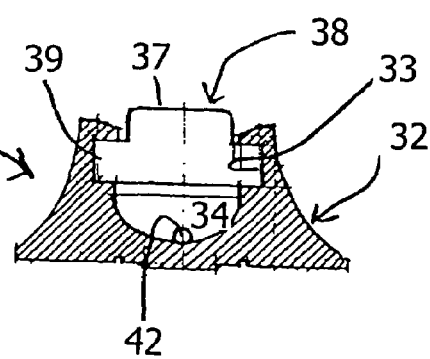
FIG. 5 is a coronal cross-sectional view of the access port apparatus of FIG. 3, taken along the line 5-5 therein, and along a vertical plane which is orthogonal to that of FIG. 4.
Figure 6:
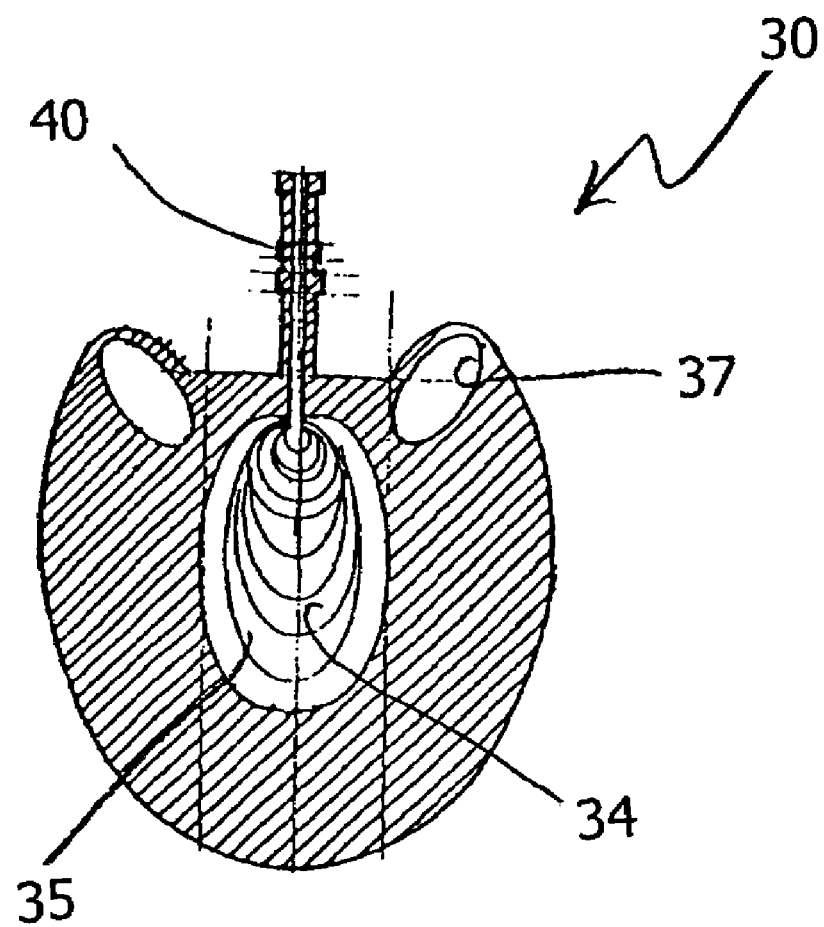
FIG. 6 is an axial cross-sectional top view of the apparatus of FIG. 3, taken along the line 6-6 in FIG. 4, and showing the directed conical shape of the chamber formed therein.

The chamber 34 has a proximal portion near the outlet and a distal portion opposite the outlet aperture 42, and is formed in an orthogonally directed conical shape, resembling a bowl portion of a bubble pipe, or an old-fashioned ear trumpet, as shown. The chamber 34 is configured with a curved inner wall 35, which slopes gradually downwardly toward an outlet aperture 42. The inner wall 35 is concavely curved to resemble the interior of a bowl, as will be seen by comparing the cross-sectional views of FIGS. 4 and 5. The main port body is configured such that when viewed in a cross-section taken along a central vertical plane, as seen in FIG. 4, the distal portion of the internal chamber 34 has a concavely curved inner surface 35 which slopes gradually downwardly below the septum 38 and which merges smoothly and uninterruptedly with the curved floor, and the proximal portion of the internal chamber 34 has an inner surface which extends toward the outlet aperture 42, such that the internal chamber 34 of the access port 30 is formed in an asymmetric curved conical shape directed substantially toward the outlet aperture 42.

The chamber 34 is shaped essentially as a substantially orthogonally directed curved funnel, to passively direct contents thereof in a curved path toward the outlet aperture 42. These contents may be fluids, such as medicines which have been injected into the chamber.

Alternatively, a tip of a guide wire 70 may be inserted into the chamber 34, and may be guided towards the outlet aperture 42 by the shape of the chamber, as will be further discussed below.

The directed conical shape of the chamber 34 promotes more complete flushing of fluids such as blood and theraputic medicated fluids therethrough, than the previously known access ports.

The main port body 32 may have one or more round or ovoid eyelets 37 formed substantially vertically through edge portions thereof, to allow tissue to grow through the port apparatus 30 and anchor it in place in a patient's body. These eyelets 37, where used, may be optionally filled with a silicone elastomeric material, to facilitate removal of the access port apparatus 30, when it is no longer needed. In either case, these eyelets 37 are designed to allow a needle to be driven through them and into tissue to tie down the port in the subcutaneous tissue The access port apparatus 30 also includes a pierceable septum 38, attached to the main port body 32 and covering the hollow chamber 34. The septum 38 is formed from a resiliently deformable material, such as a silicone elastomer. The septum 38 includes a thickened central portion 37 which is substantially cylindrical in shape, and a thinner edge portion 39 for placement in the annular channel 33, to anchor the septum in place in the main port body 32.

The access port 30 of FIGS. 3-6 also includes a hollow outlet tube 40, attached to the main port body 32. The outer surface of the outlet tube 40 is configured to retentively receive a proximal end of a catheter 75 thereon (FIG. 11). The outlet tube 40 may be integrally formed as part of the main port body 32, may be cast in place in the main port body, or may be a separate and removable piece. The outlet tube 40 is in fluid communication with the hollow chamber 34 of the main port body 32 via an outlet aperture 42 formed in the wall thereof. In the access port apparatus 30 hereof, the outlet aperture 42 is located at substantially the lowest area of the chamber 34, as shown. In the embodiment of FIGS. 3-6, it will be noted that the outlet aperture 42 is formed at the bottom of the chamber 34.

Structure of the WYR-GYD™ Needle

Figure 7:
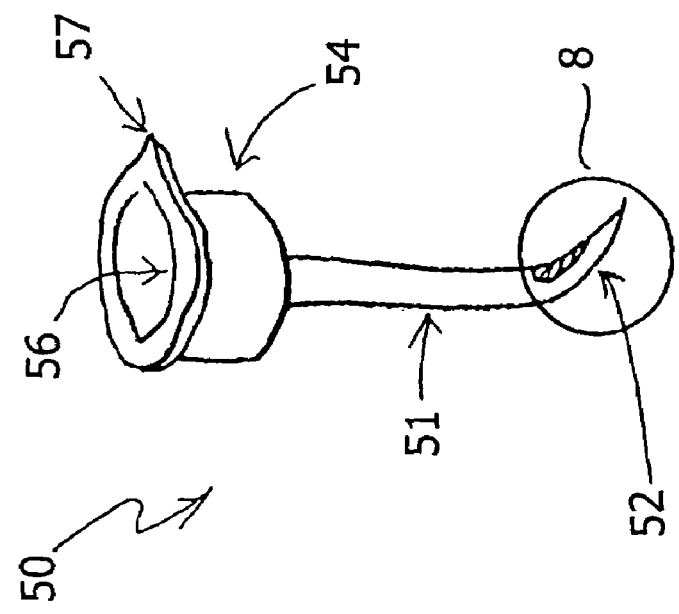
FIG. 7 is a perspective view of a specialized needle apparatus according to another aspect of the present invention.

Referring now to FIG. 7, a specialized WYR-GYD™ needle 50 is shown, which is configured to be used with the access port 30 hereof, in a method which will be subsequently described herein.

The WYR-GYD™ needle 50 includes a hollow, tubular needle body 51 with a first end and a second end opposite the first end. The first end has an access aperture 55 formed therein configured to receive a guide wire 70, as shown in FIGS. 10 and 11, and the second end of the needle is provided with a curved tip 52 having an opening 58 formed therein. The needle body 51 has a hollow passage 59 formed therein, extending from the access aperture 55 to the opening 58 of the needle tip 52. The needle 50, in the depicted embodiment, also includes a hollow receptacle body 54 having a space 56 formed therein. The receptacle body 54 is in fluid communication with the passage 59 of the needle body 51, and has a directional pointer 57 formed thereon which points in the same direction as the needle tip 52. The pointer 57 is provided to assist the user in orienting the needle 50 when it is in place in the access port 30.

Figure 8:
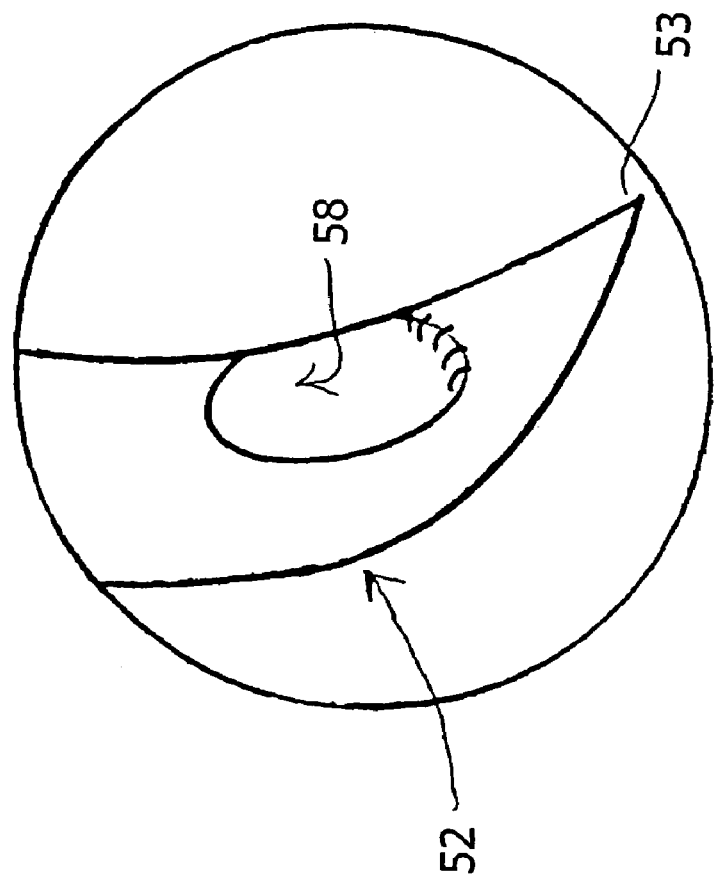
FIG. 8 is a detail view of the tip of the needle of FIG. 7, taken in the circled area 8 thereof.

Referring now to FIGS. 7-9, it will be seen that the needle tip 52 has sharply pointed extremity 53 so that the needle can pierce through skin and through the septum 38 of the access port 30. The leading part of the needle is designed not to core the septum of the port. The needle tip 52 also has an opening 58 formed therein, to allow a user to feed a guide wire 70 (FIG. 11) outwardly from the needle 50. The needle tip 52 has a non-sharp rounded lower edge portion 60 formed thereon at a lower, outwardly facing edge of the opening 58, and also has a non-sharp rounded upper edge portion 62 formed thereon at an upper, inwardly facing edge of the opening 58. These non-sharp edge portions 60, 62 are important in the practice of the present invention, because where the selected guide wire 70 has a hydrophilic coating thereon, such as the Teflon® coating on the GLIDEWIRE® brand guide wires, the rounded non-sharp edge portions 60, 62 allow such coating to slide therepast undamaged.

In contrast, if a needle having sharp edge portions were used, instead of the non-sharp edge portions 60, 62, such sharp edges could scrape the hydrophilic coating off of the guide wire, as the guide wire is extended and retracted through the needle.

Method of Using

The access port 30 hereof is specifically intended to be used in conjunction with a guide wire, according to a procedure which will be described below.

Figure 12:
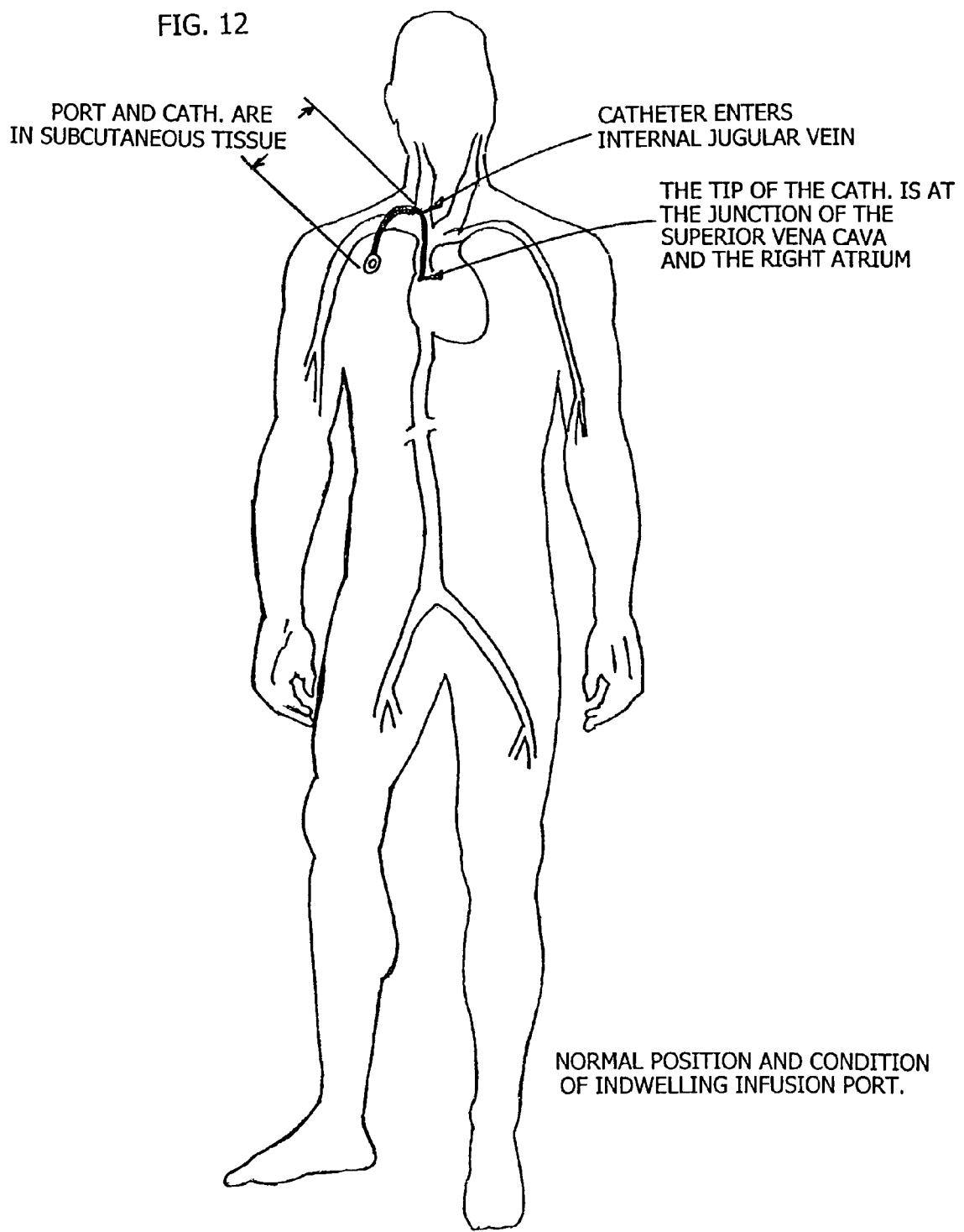
FIG. 12 is a simplified diagram of a patient's central venous system, showing a first stage of a method according to another aspect of the present invention.

The following procedure is only intended to be followed by medical professionals such as doctors, physician assistants or other specially trained and qualified medical personnel. For purposes of the present discussion, it will be assumed that the access port apparatus 30 of FIGS. 3-6 has been surgically implanted in a patient's chest or arm below the skin, and that the outlet tube 40 thereof has been connected to a catheter 75 which has been installed with its distal tip in a selected location in the patient's central venous system, such as, e.g., the superior vena cava. This arrangement of the access port 30 and catheter 75 is depicted in FIG. 12.

As a preliminary step, the area of a patient's skin which covers the port 30 must be cleansed and sterilized. Then, a specialized WYR-GYD™ needle 50 is inserted through the skin of the patient, and through the septum 38 of the access port 30, until the tip 52 of the needle 50 is inside of the port chamber 34. The WYR-GYD™ needle 50 is shown in place in the access port 30 in FIG. 10.

Once the needle 50 is in place, a guide wire is fed through the needle tip 52 and into the chamber 34. One example of a suitable guide wire which is usable in the method hereof, is the polytetrafluoroethylene-coated guide wire sold by the Terumo Medical Corporation under the trademark "GLIDEWIRE®". The guide wire is shown being threaded through the WYR-GYD™ needle, through the access port 30, and into the catheter 75 in the illustration of FIG. 11.

The orthogonally directed, conical shape of the chamber 34 passively directs the tip of the guide wire to the outlet aperture 42, and the guide wire is fed through the outlet aperture 42, through the outlet tube 40, and into the catheter 75. Since the outlet aperture 42 is located at substantially the lowest portion of the chamber 34, this makes it easier to thread the guide wire through the outlet aperture than it would otherwise be, with the previously known ports.

Figure 2:
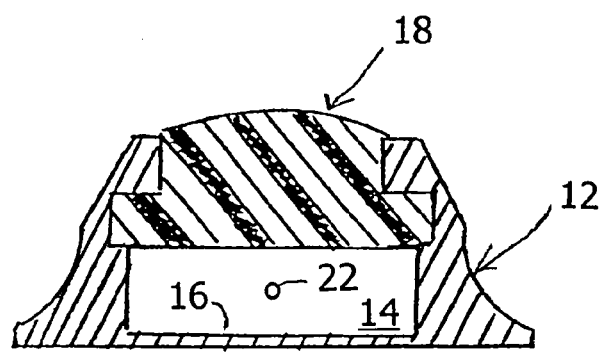
FIG. 2 is a coronal cross-sectional view of the access port apparatus of FIG. 1, taken along a vertical plane which is orthogonal to that of FIG. 1.
Figure 3:
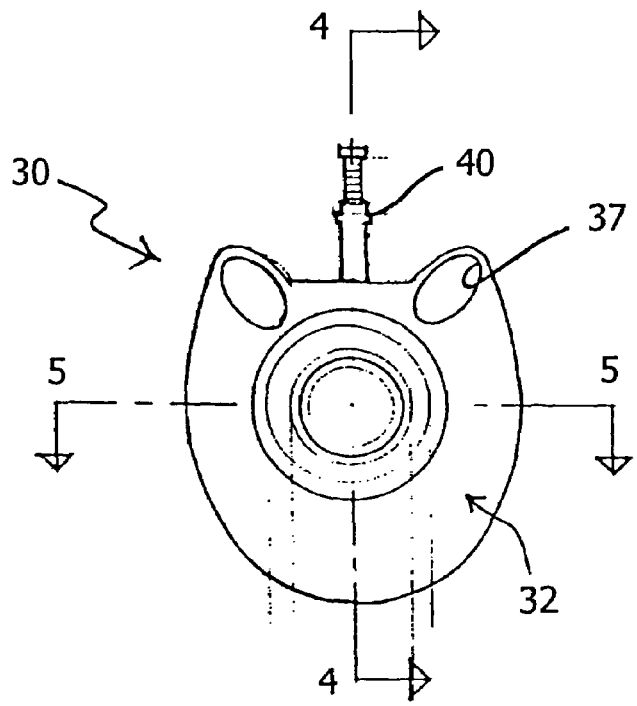
FIG. 3 is a top plan view of an access port apparatus according to a selected illustrative embodiment of the present invention.

In contrast, in the conventional access port design where the outlet aperture is situated at an elevated level in the chamber, as it is in the prior art port 10 of FIGS. 1-2, then threading a guide wire through the septum and into the outlet port is very difficult to accomplish.

Slowly and carefully, the wire tip is advanced in the catheter 75 until it reaches the tip thereof, and is then further advanced until it reaches the inferior vena cava (IVC).

If a sheath 79 is present, the guide wire tip may pierce or tear the sheath 79 as it is pushed out of the catheter tip. This movement of the guide wire through the catheter 75 helps to clean any accumulated material off the interior walls thereof, but is not a complete procedure, and may not effectively remove a sheath 79 from the catheter tip.

Figure 15:
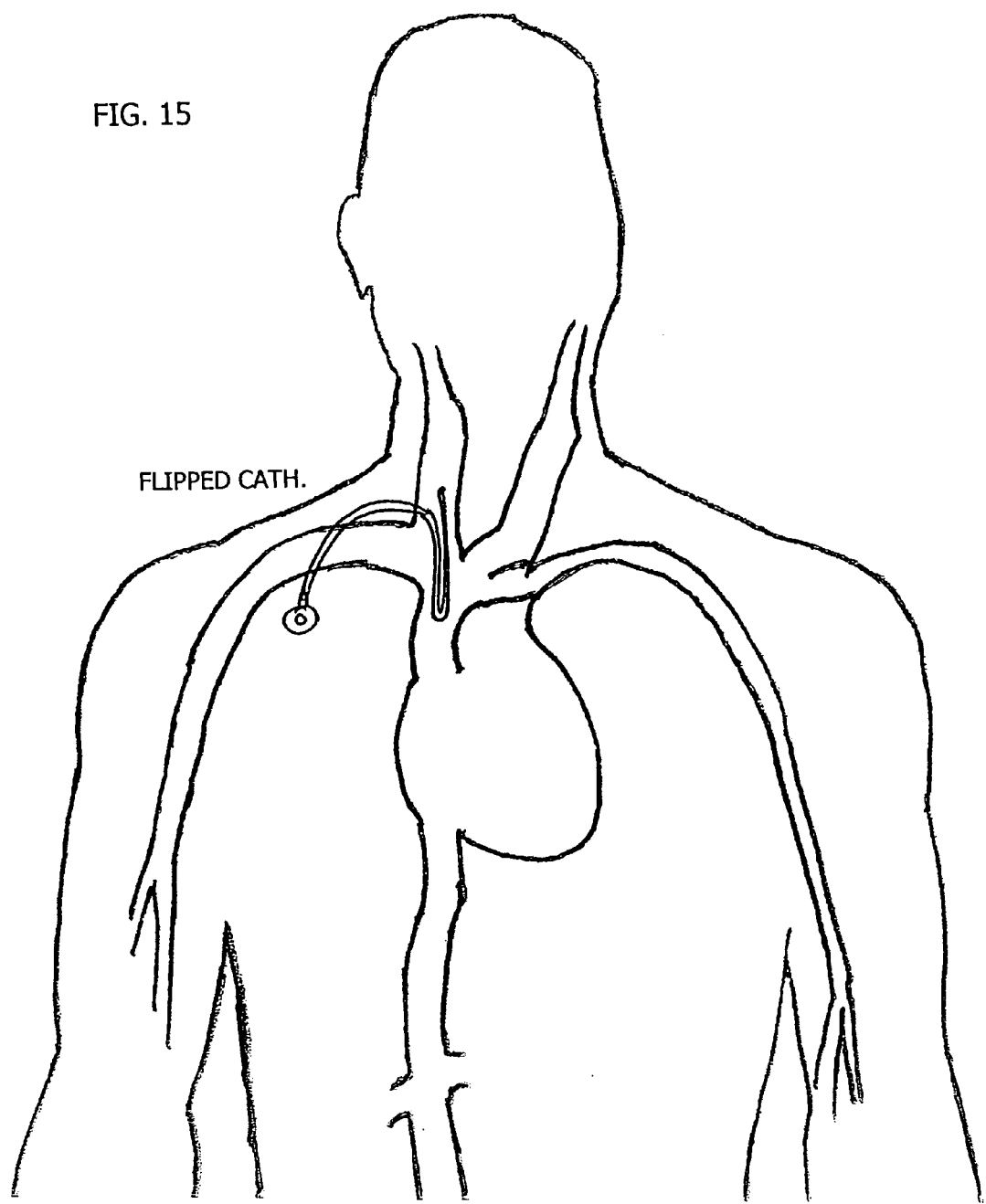
FIG. 15 is another simplified diagram of a patient's central venous system similar to FIG. 12, showing a simplified method of relocating a catheter tip according to another aspect hereof.
Figure 16:
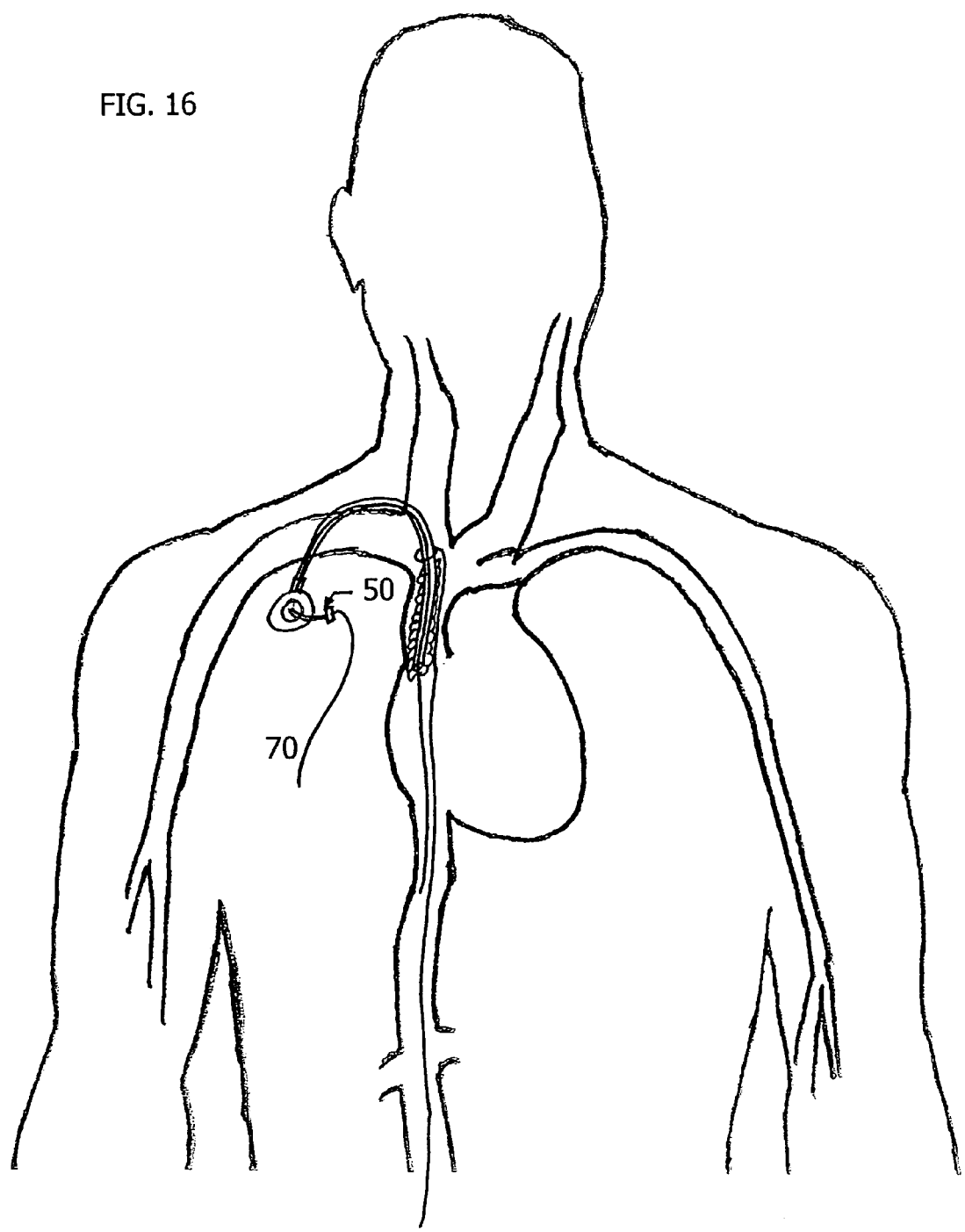
FIG. 16 is another simplified diagram of a patient's central venous system similar to FIG. 12, showing a simplified method of positioning the loop snare 77 over the catheter 75 and the fibrin sheath with the glide wire 70 in place with its distal end in the inferior vena cava.
Figure 17:
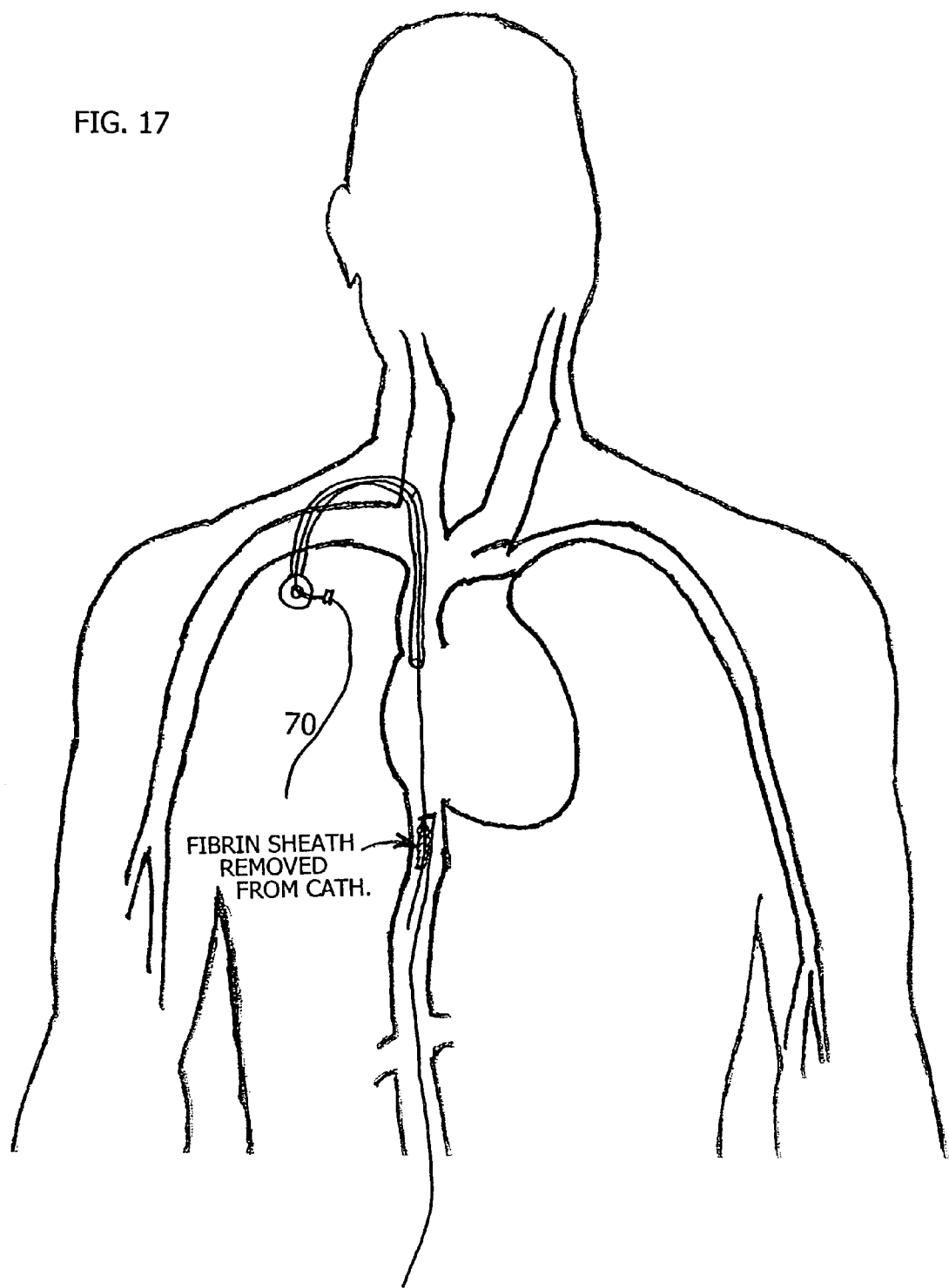
FIG. 17 is another simplified diagram of a patient's central venous system similar to FIG. 12, showing a simplified method of snaring the fibrin sheath and pulling it distally off the catheter 75.
Figure 18:
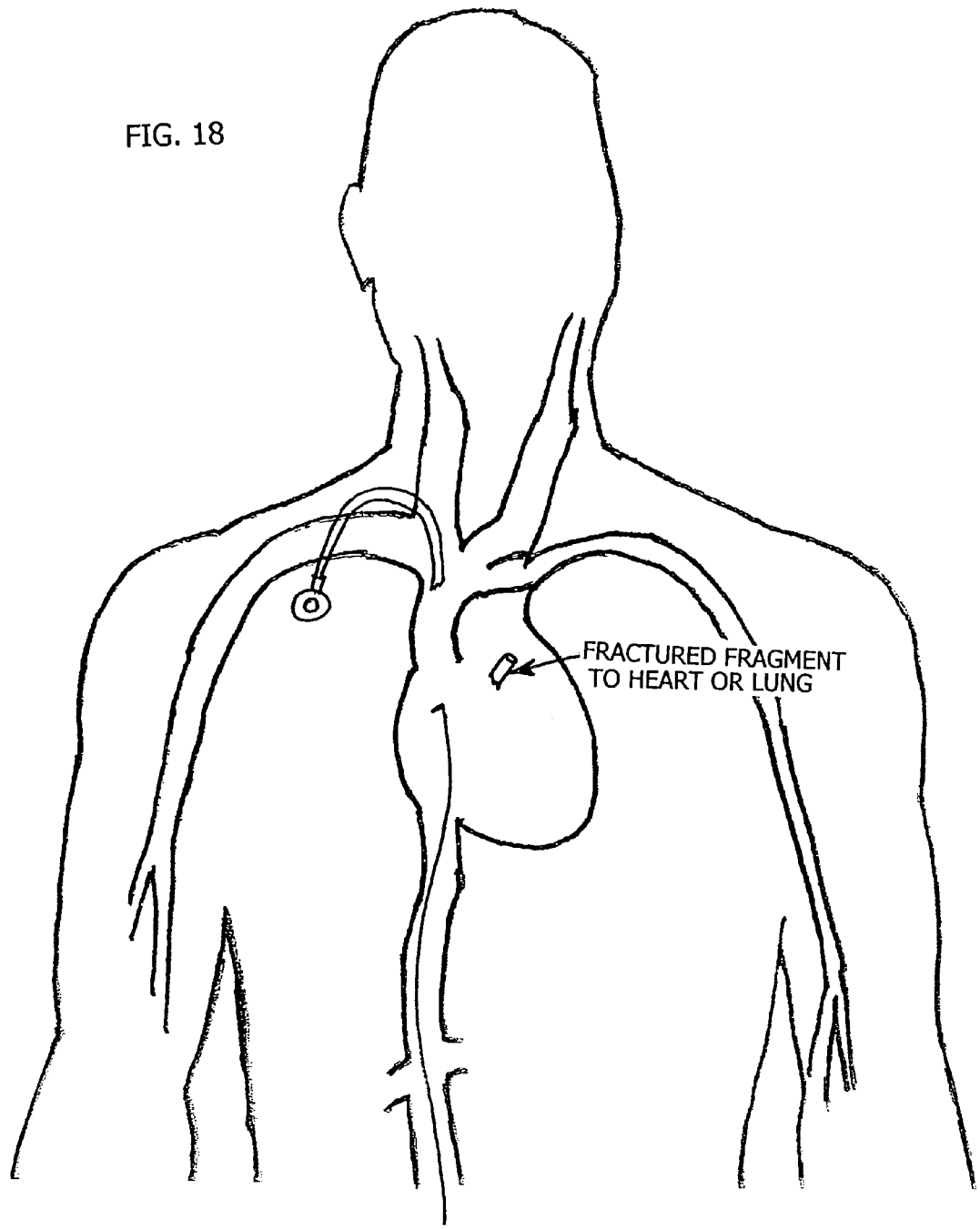
FIG. 18 is another simplified diagram of a patient's central venous system similar to FIG. 12, showing a hazard which may occur without the inventive device.

If the catheter tip has been dislodged from its normal resting place, at the junction between the superior vena cava (SVC) and the right atrium (RA), as shown in FIG. 15, then feeding the guide wire through the catheter 75 may be all that is needed to re-position the catheter tip to the SVC/RA junction.

Figure 13:
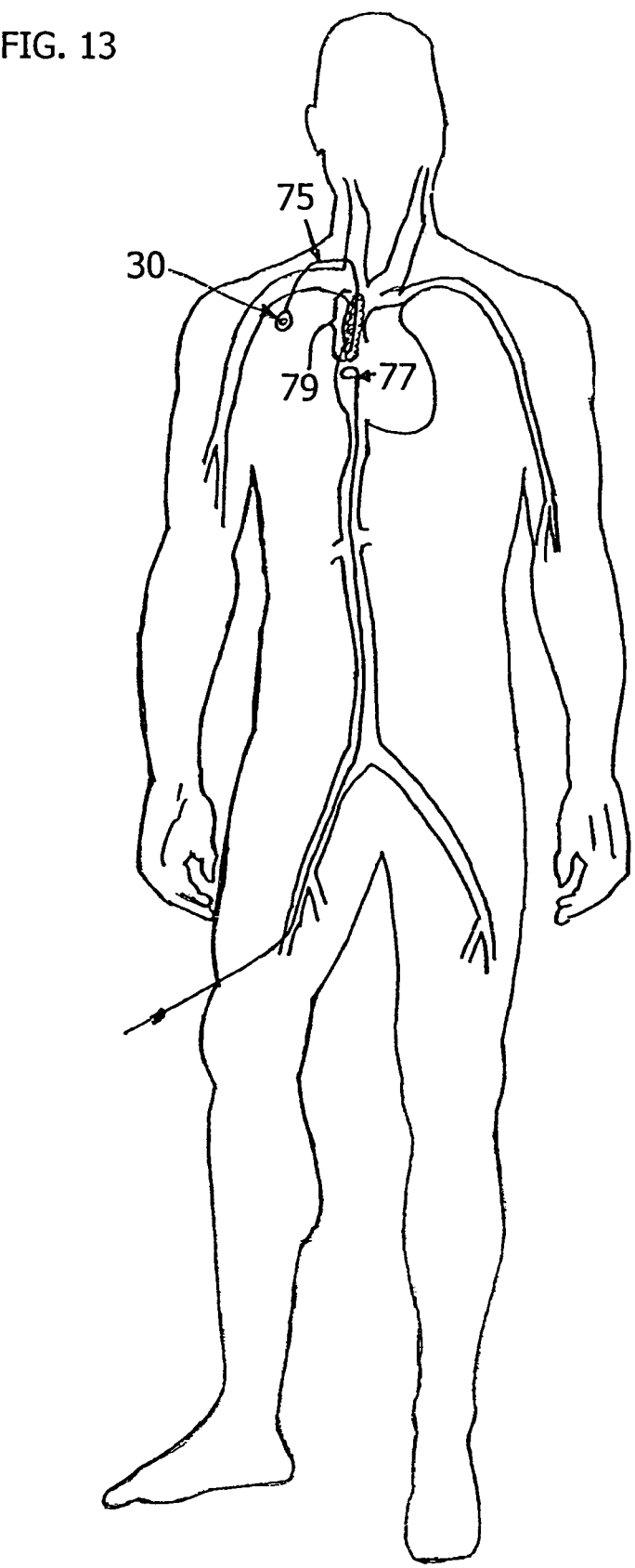
FIG. 13 is a diagram similar to FIG. 12, showing a second stage of the method.
Figure 14:
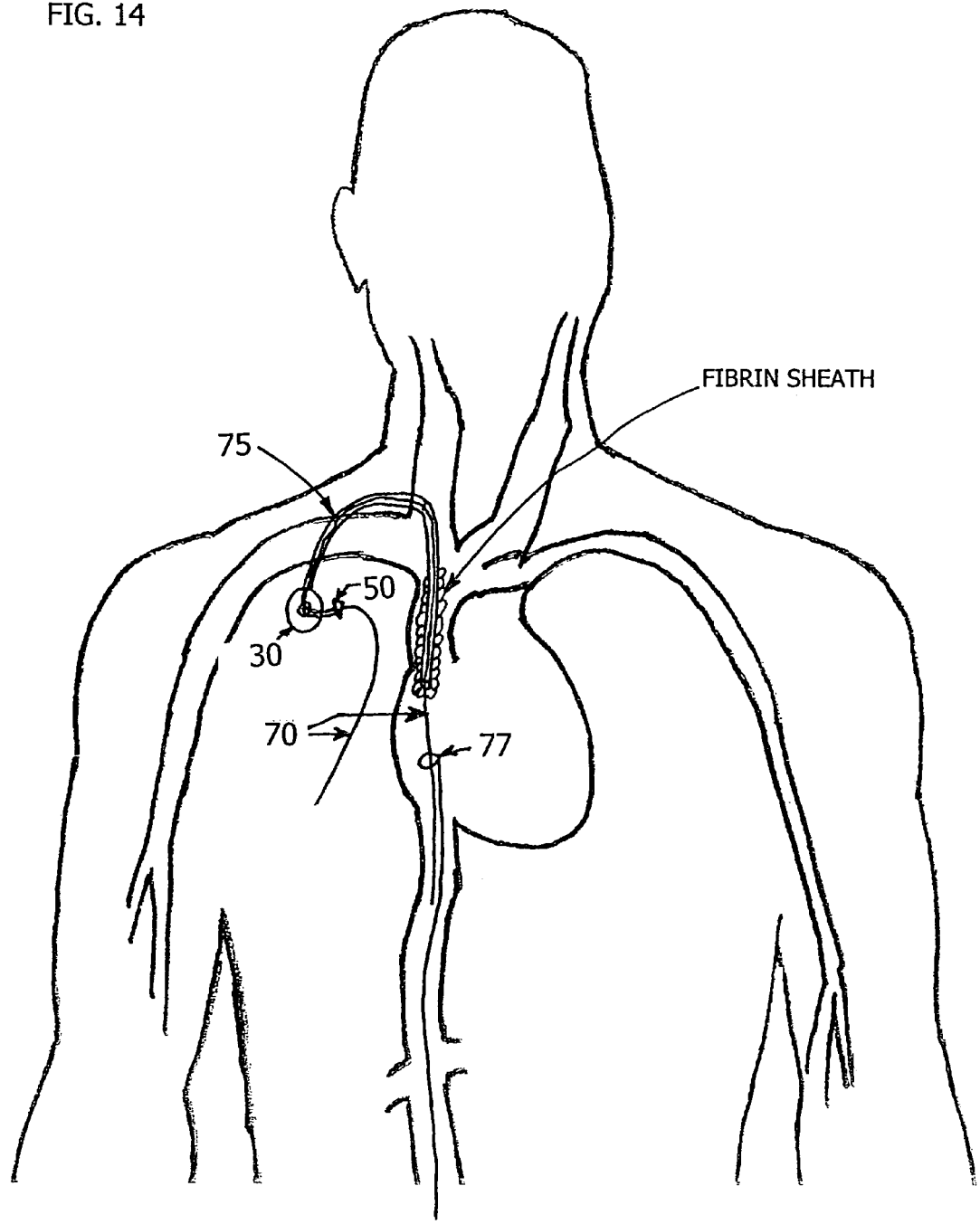
FIG. 14 is another diagram similar to FIG. 12, showing a third stage of the method.

However, if it has been determined by preliminary venogram or angiogram that a blockage, such as a sheath 79 is present on the distal portion of the catheter 75, then the next step is to access a femoral vein of the patient, and to advance a loop snare 77 through the femoral vein to the IVC. The insertion of a loop snare 77 into the femoral vein is illustrated in FIG. 13. The loop snare is then placed over the tip of the guide wire, and is advanced further, following the guide wire up the venous system, until it reaches the catheter tip. The loop snare is then placed over the sheath 79 and the catheter tip, as will be further described.

Once the loop of the loop snare reaches the tip of the catheter 75, the loop is placed over the catheter tip, and is advanced to the proximal portion of the sheath 79. The loop of the snare is then carefully tightened in place around the sheath 79 and catheter 75, and is then pulled down to the exposed guide wire, thereby slidably removing any sheath 79 covering the catheter tip. This step may be repeated two or more times, to make sure that the sheath 79 has been completely removed from the catheter 75.

If the catheter tip is broken off during this step, the broken piece is retained on the guide wire, instead of floating freely in the venous system, and this retention on the guide wire makes any broken piece more easily retrievable than a loose broken piece would be.

The sheath 79 may then be withdrawn along the guide wire, and removed from the body, by slowly withdrawing the loop snare through the femoral access site.

After the loop snare and the sheath 79 have been removed, the guide wire 70 is then removed from the patient's body. The catheter 75 and port 30 are then flushed with at least 10 ml of normal saline solution. Heparin® may be instilled into the port and catheter at this stage to resist clotting.

Finally, the specialized WYR-GYD™ needle is withdrawn from the port. The site is then covered in a sterile manner, and the patient is allowed to recuperate.

Although the present invention has been described herein with respect to a specific illustrative embodiment, the foregoing description is intended to be illustrative, and not restrictive. Those skilled in the art will realize that many modifications of the preferred embodiment could be made which would be operable. All such modifications, which are within the scope of the present disclosure, are intended to be within the scope and spirit of the present invention.

The invention claimed is:

1. An implantable vascular access port, comprising:
   a main port body having a hollow internal chamber formed therein with a curved floor at the base of the internal chamber, said main port body having an outlet formed in a side wall thereof in communication with the internal chamber, wherein the internal chamber has a proximal portion near the outlet and a distal portion opposite the outlet;
   a septum covering a surface of the main port body and formed from a flexibly resilient material; and
   a hollow outlet tube attached to the main port body and in fluid communication with the outlet thereof;
   wherein the main port body is configured such that when viewed in a cross-section taken along a central vertical plane, the distal portion of the internal chamber has a concavely curved inner surface which slopes gradually downwardly below the septum and which merges smoothly and seamlessly with the curved floor, and the proximal portion has an inner surface which extends toward the outlet, such that the internal chamber of the access port is formed in an asymmetric curved conical shape directed substantially toward the outlet, such that during a medical procedure, when a tip portion of a hollow needle is inserted through the septum, and a guide wire is fed through the needle and into the internal chamber, the shape of the internal chamber passively guides the guide wire toward the outlet.

2. The vascular access port of claim 1, wherein the main port body is provided with a concave contiguous internal surface having an asymmetrical compound curvature which slopes gradually downwardly toward the outlet.

3. The vascular access port of claim 1, wherein the internal chamber tapers toward the outlet of the main port body.

4. The vascular access port of claim 1, wherein the outlet is located proximate the floor of the internal chamber.

5. The vascular access port of claim 1, wherein the internal chamber has a central axis which curves through approximately 90 degrees between the inlet thereof and the outlet.

6. A method of using the vascular access port of claim 1, comprising the steps of:
   inserting a tip of a guide needle through the septum of the vascular port; and
   threading a guide wire through the guide needle, through the internal chamber of the access port, through the outlet, and out through the outlet tube, whereby the curved conical shape of the internal chamber facilitates alignment of the guide wire with the outlet aperture of the access port.

7. The method of claim 6, wherein the guide wire has a hydrophilic coating thereon.

8. The method of claim 6, wherein the guide wire has a hydrophilic coating thereon.

9. An implantable vascular access port, comprising:
a main port body having a hollow internal chamber formed therein with a curved floor below the internal chamber, wherein the internal chamber has a proximal portion near the outlet and a distal portion opposite the outlet, said main port body having an outlet aperture formed in a side wall thereof in communication with the internal chamber;
a septum covering a surface of the main port body and formed from a flexibly resilient material; and
a hollow outlet tube attached to the main port body and in fluid communication with the internal chamber thereof via the outlet aperture;
wherein the main port body is configured such that when viewed in a cross-section taken along a central vertical plane, the distal portion of the internal chamber has a concavely curved inner surface which slopes gradually downwardly below the septum and which merges smoothly with the curved floor, and the proximal portion has an inner surface which extends toward the outlet, such that the internal chamber tapers in an asymmetrical curved conical shape toward the outlet of the main port body,
such that during a medical procedure, when a tip portion of a hollow needle is inserted through the septum, and a guide wire is fed through the needle and into the internal chamber, the shape of the internal chamber passively guides the guide wire toward the outlet.

10. The vascular access port of claim 9, wherein the outlet aperture is located proximate the floor of the internal chamber.

11. The vascular access port of claim 9, wherein the internal chamber has a central axis which curves through approximately 90 degrees between the inlet thereof and the outlet aperture.

12. A guide needle for use in feeding a guide wire therethrough during a vascular access procedure, said guide needle comprising:
a hollow needle body having a first end and a second end opposite the first end, said first end having an access aperture formed therein configured to receive a guide wire;
said second end comprising a curved tip having an opening formed therein, said needle body having a passage formed therethrough extending from the access aperture to the opening of the tip;
wherein the opening of the needle tip has a rounded lower edge portion formed thereon at a lower, outwardly facing edge thereof, and also has a rounded upper edge portion formed thereon at an upper, inwardly facing edge of the opening,
wherein the needle tip is configured such that when a wire guide is inserted through the passage of the needle body, extended outwardly from the opening of the needle tip during a medical procedure, and is subsequently retracted back through the needle body, the wire guide contacts the rounded upper edge portion of the needle tip at the upper, inwardly facing edge of the opening during such retraction, and passes over said rounded upper edge portion substantially without interference with, or resistance from said rounded upper edge portion.

13. The guide needle of claim 12, wherein the needle further comprises a hollow receptacle body having a space formed therein, the receptacle body being attached to the needle body and in fluid communication with the passageway of the needle body.

14. The guide needle of claim 13, wherein the receptacle body has a directional pointer formed thereon which points in the same direction as the needle tip.

15. A guide needle for use in feeding a guide wire therethrough during a vascular access procedure, said guide needle comprising:
a hollow needle body having a first end and a second end opposite the first end, said first end having an access aperture formed therein configured to receive a guide wire;
said second end comprising a curved tip having an opening formed therein, said needle body having a passage formed therethrough extending from the access aperture to the opening of the tip; and
a hollow receptacle body having a space formed therein, the receptacle body attached to the needle body and in fluid communication with the passageway of the needle body;
wherein the opening of the needle tip has a rounded lower edge portion formed thereon at a lower, outwardly facing edge thereof, and also has a rounded upper edge portion formed thereon at an upper, inwardly facing edge of the opening;
wherein the needle tip is configured such that when a wire guide is inserted through the passage of the needle body, extended outwardly from the opening of the needle tip during a medical procedure, and is subsequently retracted back through the needle body, the wire guide contacts the rounded upper edge portion of the needle tip at the upper, inwardly facing edge of the opening during such retraction, and passes over said rounded upper edge portion substantially without interference with, or resistance from said rounded upper edge portion.

16. The guide needle of claim 15, wherein the receptacle body has a directional pointer formed thereon which points in the same direction as the needle tip.

17. A method of removing an accumulated sheath from a distal end of a catheter attached to an implanted vascular access port in a patient, wherein the vascular access port comprises: a main port body having a hollow internal chamber formed therein with a curved floor below the internal chamber, said main port body having an outlet formed in a side wall thereof in communication with the internal chamber, wherein the internal chamber has a proximal portion near the outlet and a distal portion opposite the outlet, a septum covering a surface of the main port body and formed from a flexibly resilient material; and a hollow outlet tube attached to the main port body and in fluid communication with the outlet thereof;
said main port body configured such that when viewed in a cross-section taken along a central vertical plane, the distal portion of the internal chamber has a concavely curved inner surface which slopes gradually downwardly below the septum and which merges smoothly with the curved floor, and the proximal portion has an inner surface which extends toward the outlet, such that the internal chamber tapers in an asymmetrical curved conical shape toward the outlet of the main port body,
said method comprising the steps of:
inserting a tip of a guide needle through a septum of the vascular port;
threading a guide wire through the guide needle, through the internal chamber of the access port, through the outlet, and out through the outlet tube, whereby the shape of the internal chamber passively guides the guide wire toward the outlet and thereby facilitates alignment of the guide wire with the outlet aperture of the access port;

extending the guide wire through the catheter and outwardly beyond the distal end of the catheter;

placing a loop of a loop snare over the sheath; and pulling the sheath off of the guide wire using the loop snare.

18. A medical kit comprising the vascular access port of claim 1, and a guide needle for use in feeding a guide wire through a vascular port, wherein the guide needle comprises a hollow needle body a hollow needle body having a first end and a second end opposite the first end, said first end having an access aperture formed therein configured to receive a guide wire;

said second end comprising a curved tip having an opening formed therein, said needle body having a passage formed therethrough extending from the access aperture to the opening of the tip;

wherein the opening of the needle tip has a rounded upper edge portion formed thereon at an upper, inwardly facing edge of the opening;

wherein the needle tip is configured such that when a wire guide is inserted through the passage of the needle body, extended outwardly from the opening of the needle tip during a medical procedure, and is subsequently retracted back through the needle body, the wire guide contacts the rounded upper edge portion of the needle tip at the upper, inwardly facing edge of the opening during such retraction, and passes over said rounded upper edge portion substantially without interference with, or resistance from said rounded upper edge portion.

* * * * *